United States Patent [19]

Anderson et al.

[11] 4,443,440
[45] Apr. 17, 1984

[54] AMINE CONTAINING ESTER PRODRUGS OF CORTICOSTEROIDS

[75] Inventors: Bradley D. Anderson, Kalamazoo; Robert A. Conradi, Portage, both of Mich.

[73] Assignee: The Upjohn Company, Kalamazoo, Mich.

[21] Appl. No.: 412,426

[22] Filed: Aug. 30, 1982

[51] Int. Cl.$^3$ .................. C07J 1/100; A61K 31/58
[52] U.S. Cl. .................. 424/243; 260/397.45
[58] Field of Search .......... 260/397.45; 424/238, 424/243

[56] References Cited

U.S. PATENT DOCUMENTS

| 3,086,011 | 4/1963 | Hull | 260/239.5 |
| 3,883,569 | 5/1975 | Phillips et al. | 260/397.45 |
| 4,221,787 | 9/1980 | Bodor | 424/241 |
| 4,242,334 | 12/1980 | Stache et al. | 424/243 |

FOREIGN PATENT DOCUMENTS

| 737501 | 4/1969 | Belgium | 260/397.45 |
| 831931 | 1/1976 | Belgium | 260/397.45 |
| 1102148 | 7/1959 | Fed. Rep. of Germany | 260/397.45 |
| 2459249 | 2/1981 | France | 260/397.45 |
| 962797 | 7/1964 | United Kingdom | 260/397.45 |

Primary Examiner—Elbert L. Roberts
Attorney, Agent, or Firm—L. Ruth Hattan

[57] ABSTRACT

Novel solution stable ester prodrugs of corticosteroids of the formula

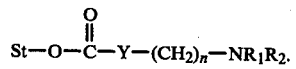

12 Claims, No Drawings

AMINE CONTAINING ESTER PRODRUGS OF CORTICOSTEROIDS

BACKGROUND OF THE INVENTION

Conventional anti-inflammatory steroids, such as cortisone, hydrocortisone, prednisone, methylprednisolone, etc., are generally poorly water soluble and therefore not suited for intravenous administration. Several types of soluble C-21 derivatives of such steroids have been disclosed in the patent literature including dicarboxylic acid hemiesters, sulfobenzoates, sulfopropionates, sulfates, phosphates, and aminoalkanoyloxy derivatives. While solubilization can generally be attained quite readily using a variety of such pro-moieties, most of the aforementioned derivatives possess other disadvantages limiting their utility as water soluble prodrugs. (The term "prodrug" denotes a derivative of an active drug which is converted after administration back to the active drug. The "pro-moiety" referred to in this application is the fragment attached to the steroid via an ester linkage and removed by ester hydrolysis in vivo.) A major problem with many common derivatives is their solution instability. Dicarboxylic acid hemiesters such as succinate esters, for example, are marketed commercially as lyophilized powders for reconstitution prior to injection due to their solution instability.

Numerous publications are available on the stability of 21-esters of corticosteroids. A partial listing of these articles and their content is given below:

*Factors Influencing Solvolysis of Corticosteroid 21-Phosphate Esters*, G. L. Flynn and D. J. Lamb, J. Pharm. Sci. 59, 1433 (1970).

*Stability of Corticosteroid Hemiesters of Dicarboxylic Acids*, E. R. Garrett, J. Pharm. Sci., 51, 445 (1962); E. R. Garrett, J. Med. Pharm. Chem., 5, 112 (1962); B. D. Anderson and V. Taphouse, J. Pharm. Sci., 70, 181 (1981); R. Yamamoto, S. Fujisawa, and M. Kawamura, Yakugaku Zasshi, 91, 855 (1971).

*Stability of Corticosteroid 21-Aminoalkylcarboxylates*, M. Kawamura, R. Yamamoto, and S. Fujisawa, Yakugaku Zasshi, 91, 863 (1971).

*Stability of Corticosteroid 21-Sulfobenzoates and 21-Sulfate*, M. Kawamura, R. Yamamoto, and S. Fujisawa, Yakugaku Zasshi, 91, 871 (1971).

Certain derivatives which do appear to exhibit sufficient solution stability may not be readily converted to the active drug in vivo. The 21-sulfate ester of hydrocortisone, for example, exhibits good solution stability but is inactive in mice. Other derivatives may possess the requisite solubility, stability, and bioconversion, but exhibit other disadvantages. Several undesirable features of phosphate esters, for example, are apparent: (1) Phosphate esters are often difficult to purify and are frequently very hygroscopic. (2) The stability of phosphate esters is optimum above pH 7 where other modes of drug degradation may be a problem. Glass surfaces are also more likely to delaminate in alkaline conditions resulting in particulate problems. (3) Precipitation of free corticosteroid due to the limited amount of hydrolysis which does occur may limit product shelf-life. Solubilization of free corticosteroid by the intact prodrug is a desirable feature which phosphate esters exhibit to only a limited extent.

The present invention provides a class of compounds which overcome these problems, providing novel solution stable prodrugs of corticosteroids.

The following patents constitute relevant prior art with respect to the compounds of the present invention: French No. 79 15286 (Derwent 23934D); U.S. Pat. No. 3,883,569 (Derwent 42064T); U.S. Pat. No. 4,242,334 (Derwent 12343B); EP No. 39 051 (Derwent 83811D); Belgium No. 737,501 (Derwent 10756R); Belgium No. 831,931 (Derwent 13049X); British No. 962,797 (CA 61:12067e); West German No. 1,102,148 (Derwent 3472); U.S. Pat. No. 3,086,011 (Derwent 7281); Japan No. 2882/63 (Derwent 7479); Japan No. 9882/63 (Derwent 8374); Japan No. 23174/63 (Derwent 9735); and U.S. Pat. No. 4,221,787. Although certain of these patents disclose in generic formulas compounds within the scope of the present invention none specifically discloses any of the presently claimed compounds.

FIELD OF INVENTION

The present invention is novel amine containing ester prodrugs of corticosteroids.

SUMMARY OF INVENTION

The compounds of the present invention are amine containing ester prodrugs of corticosteroids which are solution stable in vitro but are rapidly converted in vivo to the active parent drug and are therefore useful as anti-inflammatory agents. The compounds of the present invention are represented by the following general Formula I

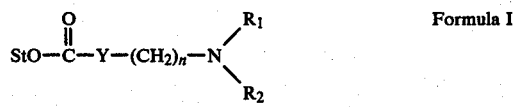

wherein

St represents a corticosteroid moiety bonded to the carbonyl via the 21-hydroxyl group of said corticosteroid; Y is a bond, —O—, or —S—;

n is an integer of from 4 to 9; and $R_1$ and $R_2$ are the same or different and represent a lower alkyl of from 1 to 4 carbon atoms which is optionally substituted by one hydroxyl group, or —$NR_1R_2$ taken together form a monocyclic heterocyclic group selected from pyrrolidino, piperidino, morpholino, thiomorpholino, piperazino and N-(lower)alkyl piperazino, preferably N-methylpiperazino.

Pharmaceutically acceptable acid addition salts and quaternary ammonium derivatives of the compounds of Formula I are also a part of the present invention.

Any reference herein to the compounds of Formula I is intended to include pharmaceutically acceptable salts and quaternary derivatives thereof.

DETAILED DESCRIPTION OF INVENTION

In the compounds of general Formula I St represents the parent corticosteroid minus the 21-hydroxyl group of said corticosteroid which is necessary to form the novel esters of the present invention. The parent corticosteroid could be depicted as StOH wherein the OH is located at the 21-position of the corticosteroid which may be depicted as follows:

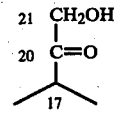

Of course the carbon atoms at positions C-17 and C-21 may be substituted as will be apparent from the description hereinbelow.

The term corticosteroid as used herein is taken to mean not only the steroids produced by the adrenal cortex but also synthetic equivalents, i.e., non-naturally occurring steroids which possess physiological properties characteristic of naturally occurring corticosteroids. Reference is made to *Drill's Pharmacology in Medicine,* McGraw-Hill Book Company, New York, (1965), Chapter 73: Adrenal Cortex and Adrenocortical Hormones, particularly pages 1185–1187 wherein typical corticosteroids employed in the present invention are described. Also, typical corticosteroids represented by StOH include those described in Applezweig, *Steroid Drugs,* McGraw-Hill Book Company, Inc., New York, 1962, pp. 435–731, and in particular the compounds associated with the following parenthetical numbers:

675; 684; 685; 734; 1030; 1033; 1034; 1035; 1036; 1038; 1039; 1048; 1051; 1052; 1059; 1061; 1063; 1064; 1066; 1067; 1068; 1070; 1071; 1072; 1073; 1078; 1080; 1082; 1083; 1084; 1086; 1087; 1088; 1092; 1093; 1094; 1095; 1099; 1100; 1101; 1105; 1107; 1108; 1109; 1110; 1111; 1112; 1116; 1116-A; 1117; 1119; 1120; 1121; 1125; 1128; 1135; 1140; 1141; 1142; 1143; 1149; 1151; 1155; 1168; 1169; 1170; 1172; 1173; 1174; 1175; 1176; 1178; 1181; 1182; 1182-A; 1183; 1184; 1186; 1187; 1189; 1193; 1194; 1197; 1198; 1206; 1207; 1214; 1215; 1216; 1217; 1218; 1220; 1221; 1226; 1227; 1230; 1231; 1242; 1243; 1244; 1246; 1248; 1251; 1270; 1272; 1273; 1274; 1275; 1279; 1280; 1281; 1282; 1283; 1285; 1286; 1287; 1294; 1295; 1296; 1306; 1307; 1308; 1319; 1320; 1322; 1323; 1324; 1325; 1327; 1328; 1329; 1330; 1331; 1333; 1334; 1336; 1337; 1338; 1339; 1340; 1350; 1351; 1352; 1363; 1368; 1370; 1385.

Also, typical corticosteroids represented by StOH include those described in Applezweig, *Steroid Drugs,* Holden-Day, Inc., San Francisco, 1964, pp. 109–438, and in particular the compounds associated with the following "catalogue" numbers:

2680; 2681; 2709; 2713; 2714; 2716; 2717; 2719; 2720; 2722; 2723; 2724; 2725; 2726; 2727; 2728; 2729; 2730; 2731; 2732; 2733; 2734; 2735; 2736; 2737; 2738; 2739; 2740; 2741; 2742; 2743; 2744; 2745; 2746; 2814; 2826; 2827; 3036-A; 3036-B; 3036-C; 3036-D; 3036-E; 3036-F; 3036-G; 3036-H; 3036-I; 3036-J; 3036-K; 3036-L; 3036-M; 3036-N; 3036-O; 3036-P; 3036-Q; 3036-R; 3036-S; 3036-T; 3036-U; 3036-V; 3052; 3054; 3057; 3071; 3073; 3074; 3075; 3078; 3081; 3082; 3087; 3088; 3090; 3108; 3109; 3109-A; 3111; 3112; 3112-A; 3114; 3117; 3118; 3119; 3119A; 3120; 3121; 3122; 3122-A; 3123; 3124; 3130; 3131; 3132; 3133; 3139; 3140; 3141; 3142; 3143; 3143-A; 3145; 3147; 3148; 3151; 3152; 3154; 3168; 3169; 3170; 3171; 3171-A; 3174; 3175; 3175-A; 3178; 3180; 3181; 3182; 3183; 3184; 3184-A; 3189; 3191; 3192; 3193; 3193-A; 3196; 3198; 3199; 3200; 3201; 3202; 3203; 3204; 3205; 3206; 3215; 3216; 3217; 3218; 3220; 3222; 3226; 3227; 3231; 3232; 3223-A; 3234; 3235; 3235-A; 3237; 3238; 3239; 3240; 3241; 3242; 3242-A; 3248; 3249; 3250; 3251; 3251-A; 3253; 3254; 3255; 3256; 3257; 3258; 3259; 3260; 3265; 3266; 3267; 3268; 3269; 3273; 3287; 3288; 3289; 3289-A; 3291; 3292; 3293; 3293-A; 3296; 3297; 3298; 3299; 3300; 3301; 3302; 3303; 3303-A; 3316; 3317; 3318; 3319; 3319-A; 3332; 3333; 3334; 3335; 3337; 3338; 3339; 3340; 3341; 3342; 3343; 3344; 3345; 3346; 3347; 3349; 3350; 3351; 3372; 3373; 3373-B; 3374; 3375; 3376; 3377; 3379.

The corticosteroid field, i.e., the compounds and their use as pharmacologically active agents is well documented, and numerous other references exist which describe the synthesis and use of corticosteroids as depicted above by StOH. Substantially any corticosteroid having a hydroxyl group at the C-21 position of the molecule is useful as the parent steroid in forming the novel esters of the present invention. The compounds of Formulas A and B represent preferred corticosteroids used to contribute the St moiety of the compounds of Formula I. Particularly preferred corticosteroids which are useful in forming the esters of Formula I are the following: hydrocortisone, cortisone, corticosterone, prednisone, prednisolone, 6α-methylprednisolone, triamcinolone, dexamethasone, flumethasone, chlorprednisone, betamethasone, 11-deoxycorticosterone, fluprednisolone, 9α-fluorohydrocortisone, fluandrenolone, paramethasone, and dehydrocorticosterone. The compounds of Formula I wherein n is 4 to 6 are more preferred. Also the compounds wherein Y is a bond are more preferred.

Lower alkyl of from 1 to 4 carbon atoms includes methyl, ethyl, n-propyl, n-butyl, and isopropyl, and when optionally substituted by one hydroxyl illustrative of such groups are 2-hydroxyethyl, 2-hydroxypropyl and 3-hydroxypropyl.

Illustrative examples of pharmaceutically acceptable acid addition salts of the compounds of Formula I are inorganic salts such as hydrochloride, hydrobromide, sulfate, phosphate; or organic salts such as acetate, malonate, succinate, or sulfonates or others as formed by treatment with a suitable acid as set forth hereinbelow.

The quaternary ammonium derivatives of the compounds of the present invention may be represented by Formula I wherein the terminal amine group is substituted by an additional group as depicted below:

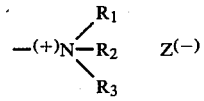

wherein $R_1$ and $R_2$ alone or taken together with the nitrogen atom to which each is attached have the meanings defined hereinabove; $R_3$ is a lower alkyl group of from 1 to 4 carbon atoms, preferably methyl or ethyl; and $Z^{(-)}$ represents an anion for example Z is I, Br, Cl, $CH_3SO_3$, or $CH_3COO$.

The compounds of the present invention are prodrugs of the corticosteroids represented by the St moiety in Formula I and have the same utility as the known or parent corticosteroid. Thus the compounds of the present invention are useful in treating warm blooded animals, e.g., dogs, cats, monkeys, horses, and particularly humans for various disease conditions. For example, the compounds of the present invention are useful in those situations where one wishes to elicit an anti-inflammatory, anti-pruritic or vasoconstrictive action inherent in the parent corticosteroid. The compounds of the present invention are particularly useful in treating acute adrenal insufficiency (Addison's disease); allergic conditions such as asthma, contact dermatitis, serum sickness, angioneurotic edema, drug hypersensitivity reactions and anaphylactoid reactions; collagen and musculoskeletal diseases, such as, rheumatoid arthritis, dermatomyositis, lupus erythematosus, rheumatic fever; dermatological diseases, such as, pemphigus and severe erythema multiforme; ulcerative colitis, and acute exacerbations of multiple sclerosis. Also when the parent corticosteroid contributing the St moiety of the compounds of Formula I possesses mineralocorticoid properties said compounds of Formula I are useful particularly in maintaining a physiological electrolyte level in patients with acute adrenal insufficiency.

Although the compounds of Formula I, salts and quaternary derivatives thereof may be administered orally, these compounds are designed for and have their primary application in those situations where oral therapy is not feasible. The compounds of the present invention are best suited for administration as sterile aqueous solutions by intravenous injection, intravenous infusion, or intramuscular or subcutaneous injection, or intravenous bolus.

The novel compounds of the present invention provide marked advantages over known corticosteroids or derivatives thereof in that these novel compounds are highly water soluble and when formulated in a manner which fully exploits the advantageous physicochemical properties of these compounds are sufficiently stable in aqueous solution to afford long term storage of solutions of said novel compounds. The compounds of the present invention are unexpectedly superior to known lower homologs, e.g., compounds of Formula I only wherein n is 1 or 2 such as the 21-diethylamino acetate or the 21-(2-diethylamino)propionate esters of hydrocortisone in that the presently claimed compounds are solution stable for much longer periods of time. Aqueous solutions of the compounds of Formula I demonstrate an increase in shelf-life over the known lower homologs of up to several hundredfold.

The solution stability of these compounds is due to several features: (1) The derivatives are highly soluble in the pH range 3.0–4.5 which is the pH range in which ester hydrolysis in aqueous solution is minimized. (2) The amino-group, which in its protonated state can strongly activate esters toward hydroxide ion catalyzed hydrolysis, is sufficiently distant from the ester linkage that its undesirable substituent effect is minimal. (3) The compounds self-associate in concentrated solutions to form molecular aggregates which increase the shelf life of formulations by (a) retarding ester hydrolysis at high concentrations, and (b) solubilizing any parent corticosteroid present in and resulting from the hydrolysis of a solution of a compound of the present invention.

Each compound of the present invention differs to some extent in the lability of its ester linkage due to variations in the electronic and steric environment contributed by the pro-moiety. In addition, factors such as pH, solution concentration, and storage temperature have a dramatic impact on the stability of formulations. However, in formulations buffered at a pH at or near the pH-hydrolysis rate minimum (3.0–4.5) and at temperatures of 25°–30° C., regardless of concentration, the compounds of the present invention are solution stable for several months. For example, a formulation of Example 1(b) prepared by dissolving the required amount of compound in buffer (acetate, 0.01μ) and diluting to give a 0.2 M solution of the ester and adjusting the pH to 4.5 using either aqueous sodium hydroxide or hydrochloric acid was estimated to have a shelf-life of 9 months at 30° C. A formulation of Example 2(c) prepared by dissolving the required amount of compound in buffer (chloroacetate, 0.01μ) and diluting to give a 0.2 M solution of the ester and adjusting the pH to 3.0 using either aqueous sodium hydroxide or hydrochloric acid was estimated to have a shelf-life of 1.5 years at 30° C. These estimates were obtained from the ratio of the solubility of the parent corticosteroid in the formulation of the prodrug over the initial rate of formulation of the parent corticosteroid in the formulation. The stability or shelf-life of solutions of compounds of the present invention can be prolonged by decreasing the storage temperature, e.g., to temperatures from 4° to 24° C.

As indicated previously, the compounds of the present invention exhibit stability in water only when the pH of their solution is properly controlled. Ideally, the pH will be maintained at a level where the hydrolysis of the ester is at a minimum. This minimum depends to a certain degree on the chemical structure of the promoiety, the formulation concentration, and the temperature of storage but in general will be at a pH of about 3.0 to 4.5 for the compounds of this invention. Most advantageously, buffers should be employed to maintain the pH at or near the desired level throughout the shelf life of the formulation. Suitable buffers are those which are physiologically acceptable and exhibit sufficient buffer capacity in the pH range 3.0–4.5, e.g., acetate, citrate, succinate, or phthalate buffers and the like. The quantity of buffer used is determined by means known in the art and will depend on the pH desired, the concentration of the solution, and the buffering capacity of the buffer.

The concentration of the solution stable formulations of the compounds of Formula I depends on the activity level of and the ultimate dose of parent corticosteroid desired. In general the stability of the formulations increases as the concentration of novel ester increases. In essence the solution stable formulations may be as concentrated as viscosity properties permit or until the solubility of the novel ester is exceeded. Inasmuch as the compounds of the present invention are converted to the parent corticosteroid in vivo, ideally the concentration of the novel ester and the volume of the solution administered will be chosen to provide a quantity of parent corticosteroid which is known to be effective. For example, a 0.267 M solution of the compound in Example 1(b), set forth below, is equivalent to 100 mg/ml of 6α-methylprednisolone.

Sterile aqueous solutions of the compounds of Formula I typically will contain other components such as preservatives, anti-oxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Typical formulations useful in practicing the present invention are set forth below.

To demonstrate the bioconversion of the compounds of the present invention to the parent steroid in serum, samples of human serum from males and from females were spiked with approximately 10 μg/ml of the compounds of Example 1(b) or Example 2(c) and warmed to 37° C. in a water bath. Aliquots of 200 μl each were withdrawn at timed intervals and quenched with 10 ml of 18% methanol, 1.2% acetic acid and water and analyzed using HPLC. The half-life of the novel ester for conversion to the parent steroid was calculated from a plot of parent steroid concentration against time. The averages of the half-life for the compounds of Example 1(b) and Example 2(c) as determined in serum were 34 minutes and 6 minutes, respectively.

The compounds of the present invention may be prepared by various means, and it will be apparent from the following that the ester moiety attached at the 21-position of the steroid, St, may be introduced by reaction of the steroid with an appropriate starting material amine which provides the entire moiety, or said ester moiety may be introduced by a sequence of one or more reactions.

In preparing the compounds of Formula I wherein Y is oxy, i.e., —O—, equimolar amounts of an amine of the formula

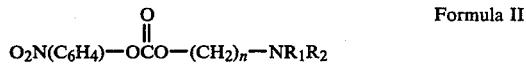

Formula II wherein ($C_6H_4$) is 1,4-phenylene and n, $R_1$ and $R_2$ have the meanings defined in Formula I, and a parent steroid of the formula StOH wherein St has the meaning defined in Formula I are reacted in a dry aprotic solvent such as tetrahydrofuran (THF), dimethylformamide (DMF) or dimethylsulfoxide (DMSO), in the presence of a tertiary amine (preferably pyridine) and an acylation catalyst such as dimethylaminopyridine (DMAP) or N-methylimidazole. Although the reaction may be performed at room temperature it is convenient to gently warm the reaction mixture to about 50°–60° C. with stirring until all the activated carbonate ester is consumed. The product is isolated by pouring the reaction mixture into water with the pH adjusted to 2–4, washing with an organic solvent, e.g., ether or ethyl acetate, then quickly adjusting the pH to 7–8 and extracting with an organic solvent such as ethyl acetate. The product is isolated by removing the solvent and purified by recrystallization or chromatographic techniques.

To prepare compounds of Formula I wherein Y is sulfur, i.e., —S—, equimolar quantities of an appropriate thiol amine of the formula

Formula III wherein n, $R_1$ and $R_2$ have the meanings defined in Formula I, and a chloroformate derivative of the parent steroid represented by the formula

Formula IV wherein St has the meaning defined in Formula I with an equivalent quantity of a tertiary amine, such as triethylamine, are reacted in a dry aprotic solvent such as, THF, DMF or DMSO. The reaction mixture may be warmed gently if desired. The product is isolated by extraction from water with an organic solvent such as ethyl acetate and purified by crystallization or chromatography.

The compounds of Formula I wherein Y is a bond are prepared by reacting equimolar amounts of an amino acid of the formula

Formula V wherein n, $R_1$ and $R_2$ have the meanings defined in Formula I with a 21-iodo or 21-O-mesyl derivative of the parent steroid which may be represented respectively by the formulas

     Formula VI and

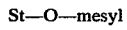     Formula VIII wherein St has the meaning defined in Formula I and mesyl means —$S(O_2)$—$CH_3$. When the 21-iodo steroid derivative is employed the reaction proceeds at room temperature, whereas when the 21-O-mesyl steroid derivative is used the reaction is heated. Preferably both reactions are heated to about 60°–70° C. The reaction is carried out in a dry aprotic solvent such as DMF in the presence of a sterically hindered tertiary amine such as diisopropylethylamine. The product is isolated by extraction from water with an organic solvent, suitably ethyl acetate, and purified by recrystallization or chromatography.

To form acid addition salts of the compounds of Formula I said compounds are treated with suitable pharmaceutically acceptable inorganic or organic acids by standard procedures. Suitable inorganic acids are, for example, hydrochloric, hydrobromic, nitric, sulfuric or phosphoric acids. Suitable organic acids include carboxylic acids, such as, acetic, propionic, glycolic, lactic, pyruvic, malonic, succinic, fumaric, malic, tartaric, citric, ascorbic, maleic, hydroxymaleic, benzoic, hydroxybenzoic, phenylacetic, glutamic, glutaric, cinnamic, salicylic, or sulfonic acids such as methane sulfonic, toluenesulfonic, or 2-hydroxyethanesulfonic.

The quaternary ammonium salts of the compounds of Formula I are formed by contacting said compounds with a suitable alkylating agent such as dimethyl sulfate, diethyl sulfate, or a suitable alkyl halide such as methyl or ethyl chloride or methyl or ethyl bromide or methyl or ethyl iodide.

The compounds of Formula II are prepared by reacting an amino alkanol of the formula HO($CH_2$)$_n$—$NR_1R_2$ wherein n, $R_1$ and $R_2$ are as defined in Formula I with p-nitrophenylchloroformate in a dry aprotic solvent, such as, THF in the presence of an amine, such as, triethylamine. The amino alkanol compounds are known in the art or are prepared by generally known procedures by treatment of an appropriate ω-iodoalkanol with an amine of the formula $NHR_1R_2$ wherein $R_1$ and $R_2$ are as defined in Formula I.

The compounds of Formula III are prepared by reacting equimolar amounts of an ω-haloalkylamine of the formula halo—($CH_2$)$_n$—$NR_1R_2$ wherein halo is halogen and n, $R_1$ and $R_2$ are as defined in Formula I and thiourea in propylene glycol at an elevated temperature. When the halide has been displaced, the isothiouronium salt is cleaved by adding an amine such as tetraethylene pentamine and continuing to apply heat. When the free thiol has formed, this product is isolated by extractive means or by distillation under reduced pressure.

The steroid chloroformates of Formula IV are prepared by reacting the parent 21 hydroxy steroid with a molar excess of phosgene in THF in a chilled reaction vessel which is then allowed to warm to room temperature venting excess phosgene through a NaOH trap. After about one hour the solution is concentrated under reduced pressure and the chloroformate precipitates out.

The compounds of Formula V are known in the art or are prepared by procedures well known in the art.

The ω-haloamines employed hereinabove are obtained by adding a secondary amine of the formula $HNR_1R_2$ wherein $R_1$ and $R_2$ are as defined in Formula I portionwise to a molar excess of an appropriate α,ω-alkylenedihalide. Generally the reaction mixture is heated and if the halide is chloride, an iodide salt may be added as a catalyst.

The following examples further illustrate the invention.

EXAMPLE 1

(a) Diethylaminocaproic acid

To 100 ml (1 mole) of diethylamine was added dropwise 15 ml (0.1 mole) of 6-bromocaproic acid with stirring. Stirring was continued for 2 hours at 25° C. during which time a crystalline solid (diethylamine hydrobromide) began to precipitate. After 1.5 additional hours at 45° C. the reaction appeared to be complete with no starting material or other amine-free products evident by thin layer chromatography (silica gel, ethyl acetate+5% acetic acid). After some of the excess diethyl amine was filtered out as the hydrobromide salt, the reaction mixture was concentrated to an oil. About half of this oil was dissolved in water, adjusted to pH 12 and loaded onto an anion exchange column in the hydroxide form. The column was eluted first with about 3 column volumes of deionized water then with 1 N HCl. The pH of the effluent was monitored and the fractions beginning where the pH dropped drastically were collected. These fractions were combined, adjusted to pH 7.7 with NaOH, and concentrated under vacuum to an oil. The oil was dissolved in acetonitrile, which resulted in precipitation of NaCl. Concentrating the supernate under reduced pressure gave the title product as a neutral oil.

(b) Methylprednisolone 21-(6-diethylamino)caproate HCl

A mixture of 2.5 g (12 mmol) of the amino acid (as the zwitter-ion) obtained in Example 1(a) and 4.84 g (10 mmol) of methylprednisolone 21-iodide in 30 ml of dry dimethylformamide (DMF) was stirred under $N_2$ for one hour at 75° C. Product formation, monitored by high pressure liquid chromatography, was 90% complete after 40 minutes.

The reaction mixture was partitioned between 250 ml ethyl acetate and 250 ml dilute HCl. The aqueous phase was collected and stirred with 250 ml ethyl acetate while adjusting to pH 8.0. This organic extract was dried over $MgSO_4$ and rotovaped to an oil. The oil was taken up in butylchloride. A small quantity of brownish solid precipitate formed and was removed. The remaining solution was then stripped of solvent, taken up in THF and titrated with 1 N HCl. After solvent was removed under vacuum and excess water was removed as an acetonitrile azeotrope, the remaining gum was triturated several days with ethyl ether producing a white free flowing solid. This material was recrystallized from isopropanol/butylchloride and dried at 60° C. under vacuum, yielding crystalline title product.

Analysis: $C_{32}H_{49}NO_6 \cdot HCl$. Calculated: C, 66.24; H, 8.69; N, 2.41; Cl, 6.11. Found: C, 65.95; H, 8.68; N, 2.05; Cl, 6.03.

$KF(H_2O)$: 0.15%.

M.P.: 161.5–163.5.

EXAMPLE 2

(a) 6-(Diethylamino)hexanol

A mixture of 10 ml (75 mmol) of 6-chlorohexanol and 16.9 g (112 mmole) of NaI dissolved in 100 ml acetone was refluxed for 3.5 days. The reaction mixture was filtered and the filtrate was concentrated to an oil and dissolved in 100 ml of ether. The ether solution was filtered, concentrated to an oil, and dissolved in 30 ml of diethylamine. The solution was stirred for 4 hours and filtered. The filtrate was concentrated to an oil, taken up in acidified water (pH<2) and washed with ethylacetate. The acidic solution was then adjusted to pH 9.5 and extracted twice with ethyl acetate. The organic extract was dried over $MgSO_4$ and concentrated under vacuum to yield 7.5 g of the title compound as an oily product.

(b) p-Nitrophenyl, 6-(diethylamino)hexanol carbonate

A mixture of 4.32 g (25 mmole) of 6-diethylaminohexanol and 5.04 g (25 mmole) of p-nitrophenylchloroformate in 40 ml of dry THF was stirred for about 30 minutes after which 2 ml of triethylamine was added resulting in copious precipitate formation. An additional 2 ml of triethylamine was added, and after stirring 15 minutes the mixture was filtered. The filter cake was washed with THF, the washings were added to the filtrate, and the combined THF solutions were rotovaped to an oil. Thin layer chromatography at this point showed that the desired product made up at least 80% of the oil, the rest being bis(p-nitrophenyl)carbonate. This oil was used without further purification for the next step in the reaction.

(c) Methylprednisolone, 21-[6-(diethylamino)hexyl carbonate], sulfate(2:1)

The oil obtained in Example 2(b) above and 5.6 (15 mmole) of methylprednisolone were combined in 200 ml of dry THF and 0.8 g of dimethylaminopyridine (DMAP) was added. This solution was concentrated to 50 ml and stirred at room temperature overnight. High pressure liquid chromatographic analysis of the reaction mixture (RP-8 column, 45% $CH_3CN$, 55% $H_2O$, 0.03 M HOAc, pH 5, 0.02% DMOA, flow rate 2.5 ml/min) showed, in addition to the desired product, some unreacted phenyl carbonate. The phenyl carbonate was selectively hydrolyzed in a THF/water solution containing about 1 mg/ml imidazole at pH 7.7. This solution was then concentrated under reduced pressure to an oil. The oil was taken up in ethyl acetate to which hexane was added and the cloudy solution was shaken with water adjusted to pH 3. The aqueous phase was then separated and stirred with an equal volume of ethyl acetate while adjusting pH to 7.5 with 1 N NaOH. The ethyl acetate solution was then separated, concentrated to an oil, and taken up in THF and 10% water. This solution was titrated to an endpoint with 10.3 ml of 1 N HCl. The titrated solution was stripped of solvent, using acetonitrile to remove residual water as the azeotrope. The oil was triturated with ether yielding 6 g of white solid. The solid was redissolved in 150 ml boiling acetonitrile from which 3.5 g of crystalline solid precipitated. This solid was pure by thin layer chromatography. A portion of the HCl salt was converted back to the free base and titrated with $H_2SO_4$ to give the sulfate salt. The sulfate was obtained as a crystalline solid by first triturating the crude oil with ether to give an amorphous solid then treating this solid with hot acetonitrile.

Analysis for $C_{33}H_{51}NO_7$ HCl: Theory (corrected for 2.3% $H_2O$): C, 63.50; H, 8.65; N, 2.24; Cl, 5.68. Found: C, 63.93; H, 8.44; N, 2.13; Cl, 5.74. M.p. 204.5°–205.0° C.

Analysis for $(C_{33}H_{51}NO_7)_2$ $H_2SO_4$: Theory (corrected for 2.25% $H_2O$): C, 62.21; H, 8.48; N, 2.20; S, 2.51. Found: C, 62.22; H, 8.25; N, 2.18; S, 2.47. M.p. 183.3°–184.3° C.

EXAMPLE 3

(a) When in the procedure of Example 1(a) an appropriate amount of 5-bromovaleric acid is substituted for 6-bromocaproic acid, diethylaminovaleric acid is obtained.

(b) When in the procedure of Example 1(b) an appropriate amount of diethylaminovaleric acid is substituted for diethylaminocaproic acid, methylprednisolone 21-(5-diethylamino)valerate HCl is obtained.

EXAMPLE 4

When in the procedure of Examples 1(b) and 3(b) hydrocortisone 21-iodide is substituted for methylprednisolone 21-iodide the following compounds are obtained:
hydrocortisone 21-(6-diethylamino)caproate HCl;
hydrocortisone 21-(5-diethylamino)valerate HCl.

EXAMPLE 5

Dexamethasone, 21-[6-(dipropylamino)hexyl thiocarbonate], hydrochloride

To a solution of 61 g of 1,6-dibromohexane in 200 ml DMF is added dropwise with stirring 7 ml dipropylamine. The reaction mixture is allowed to stand until the free amine is consumed. Excess solvent is then removed on a rotary evaporator and the residue is partitioned between ethylacetate and water at pH 3. Unreacted dihalide is removed in the organic solvent and discarded. The product in water is adjusted to pH 9 and extracted into ethylacetate. The solvent is then removed by rotary evaporation leaving purified 6-(dipropylamine)hexyl bromide as an oil residue.

The oil residue is dissolved in 50 ml propylene glycol and treated with 3.8 g of thiourea with heating and vigorous stirring. When the reaction is complete, 5 ml of tetraethylene pentamine is added to the solution and heating is continued until the isothiouronium salt is all converted to the thiol. The thiol is isolated by diluting the reaction mixture with 500 ml of water adjusted to pH 3, washing this solution with ethylacetate, adjusting the pH up to 9, and extracting the thiol into ethylacetate. The solvent is removed under reduced pressure before the coupling step.

A solution of 10 g of dexamethasone in 100 ml of THF is treated with 10 ml of phosgene while cooling in a dry-ice acetone bath. The reaction vessel is allowed to come to room temperature, venting excess phosgene through a sodium hydroxide trap, and after one hour the solution is concentrated under reduced pressure to about 30 ml. The dexamethasone 21-chloroformate is isolated by filtration after it crystallizes out of solution. The final coupling reaction is accomplished by heating the above-obtained thiol with the chloroformate in THF under nitrogen. The title product is isolated by extractive procedures. It is most convenient to purify the product as the hydrochloride salt.

EXAMPLE 6

When in the procedure of Example 1(b) an appropriate amount of the 21-iodide of triamcinolone, dexamethasone, flumethasone, chlorprednisone, betamethasone, flurandrenolone, prednisone, fluprednisolone, cortisone, corticosterone, 11-deoxycorticosterone, 9α-fluorohydrocortisone, dehydrocorticosterone, or paramethasone is substituted for methylprednisolone 21-iodide the following respective products are obtained as the hydrochloride salt:
triamcinolone, 21-(6-diethylamino)caproate,
dexamethasone, 21-(6-diethylamino)caproate,
flumethasone, 21-(6-diethylamino)caproate,
chlorprednisone, 21-(6-diethylamino)caproate,
betamethasone, 21-(6-diethylamino)caproate,
flurandrenolone, 21-(6-diethylamino)caproate,
prednisone, 21-(6-diethylamino)caproate,
fluprednisolone, 21-(6-diethylamino)caproate,
cortisone, 21-(6-diethylamino)caproate,
corticosterone, 21-(6-diethylamino)caproate,
11-deoxycorticosterone, 21-(6-diethylamino)caproate,
9α-fluorohydrocortisone, 21-(6-diethylamino)caproate,
dehydrocorticosterone, 21-(6-diethylamino)caproate,
paramethasone, 21-(6-diethylamino)caproate.

The following examples are illustrative of typical formulations of representative compounds of the present invention.

EXAMPLE 7

| | |
|---|---|
| Methylprednisolone, 21-[6-(diethylamino)hexyl carbonate], sulfate (2:1) | 166.3 mg |
| (Equivalent to 100 mg methylprednisolone) | |
| Dilute $H_2SO_4$ or NaOH to adjust pH to 3.0–3.5 | |
| Sterile water for injection to make 1 ml | |

EXAMPLE 8

| | |
|---|---|
| Methylprednisolone, 21-(6-diethylamino)caproate HCl | 155.0 mg |
| (Equivalent to 100 mg methylprednisolone) | |
| Acetic acid | 2.3 mg |
| Sodium acetate | 1.0 mg |
| Benzyl alcohol | 8.8 mg |
| HCl (dilute) or NaOH (dilute) to adjust pH to 4.25 | |
| Sterile water for injection to make 1 ml | |

EXAMPLE 9

| | |
|---|---|
| Dexamethasone, 21-(5-diethylamino)valerate HCl | 30.0 mg |
| (Equivalent to 20 mg dexamethasone) | |
| Creatinine | 8.0 mg |
| Acetic acid | 4.6 mg |
| Sodium acetate | 2.0 mg |
| Sodium bisulfite | 1.0 mg |
| Disodium edetate | .5 mg |
| Methylparaben | 1.5 mg |
| Propylparaben | .2 mg |
| HCl (dilute) or NaOH (dilute) to adjust pH to 4.25 | |
| Water for injection to make 1 ml | |

FORMULA CHART

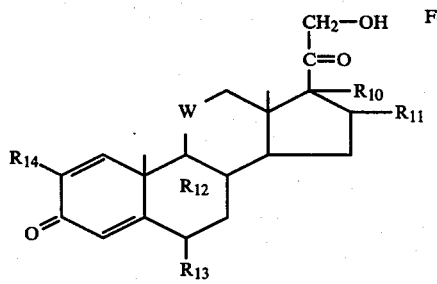

Formula A

In the above Formula A:
W is

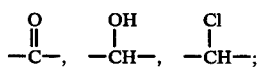

$R_{10}$ is H,α—OH;
$R_{11}$ is H, α—CH$_3$, β—CH$_3$, α—F, β—F, α—OH or =CH$_2$;
$R_{12}$ is H, F, Cl, Br;
$R_{13}$ is H,α—F, α—CH$_3$, β—CH$_3$, α—Cl, β—Cl, β—OH;
$R_{14}$ is H,CH$_3$.

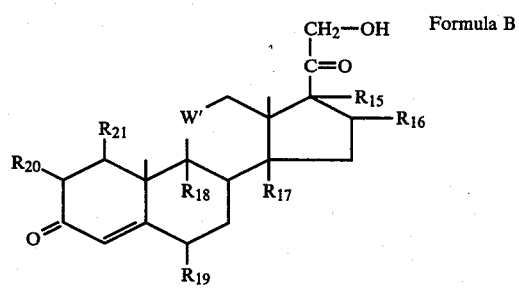

Formula B

In the above Formula B:
W' is

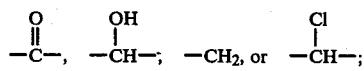

$R_{16}$ is H, α—OH, α—CH$_3$;
$R_{17}$ is H, α—OH;
$R_{18}$ is H, α—F, β—F, α—Br, α—Cl, α—OH;
$R_{19}$ is H, β—OH, α—CH$_3$, β—CH$_3$, α—F, α—Cl,
$R_{20}$ is H, α—F, Cl, α—CH$_3$, =CH$_2$;
$R_{21}$ is H, α—OH; with the proviso that one of $R_{20}$ and $R_{21}$ is hydrogen;
preferably $R_{17}$, $R_{20}$ and $R_{21}$ are hydrogen.

We claim:
1. A compound of the formula

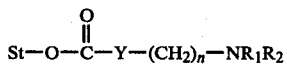

wherein
St is a corticosteroid absent the C-21 hydroxyl of said corticosteroid;
Y is a bond, —O— or —S—;
n is an integer of form 4 to 9;
each of $R_1$ and $R_2$ is a lower alkyl group of from 1 to 4 carbon atoms optionally substituted with one hydroxyl group, or $R_1$ and $R_2$ taken together with the nitrogen atom to which each is attached forms a monocyclic heterocyclic ring selected from pyrrolidino, piperidino, morpholino, thiomorpholino, piperazino, or N-(lower)alkyl piperazino; pharmaceutically acceptable addition salts and quaternary ammonium salts thereof.

2. A compound of claim 1 wherein n is 4 to 6.
3. A compound of claim 2 which is methylprednisolone, 21-[6-(diethylamino)hexyl carbonate], sulfate.
4. A compound of claim 2 wherein Y is a bond.
5. A compound of claim 2 wherein the corticosteroid forming the St moiety is 6α-methylprednisolone, cortisone, hydrocortisone, corticosterone, prednisone, prednisolone, triamcinolone, dexamethasone, flumethasone, chlorprednisone, betamethasone, 11-deoxycorticosterone, flurandrenolone, fluprednisolone, 9α-fluorohydrocortisone, paramethasone or dehydrocorticosterone.
6. A compound of claim 5 which is methylprednisolone, 21-(6-diethylamino)caproate or a pharmaceutically acceptable salt thereof.
7. A compound of claim 5 which is methylprednisolone, 21-(5-diethylamino)valerate or a pharmaceutically acceptable salt thereof.
8. A compound of claim 5 which is hydrocortisone, 21-(5-diethylamino)valerate or a pharmaceutically acceptable salt thereof.
9. A pharmaceutical composition comprising an effective quantity of a compound of claim 1 as a sterile aqueous solution.
10. A composition of clam 9 which is in unit dosage form.
11. A composition of claim 9 or 10 wherein the compound is
methylprednisolone, 21-(6-diethylamino)caproate,
methylprednisolone, 21-(5-diethylamino)valerate,
hydrocortisone, 21-(5-diethylamino)valerate,
methylprednisolone, 21-[5-(diethylamino)hexyl carbonate], sulfate
or a pharmaceutically acceptable salt thereof.
12. A compound of claim 1 wherein n is 5 or 6.

* * * * *

Disclaimer 4,443,440.—*Bradley D. Anderson*, Kalamazoo; and *Robert A. Conradi*, Portage, Mich. AMINE CONTAINING ESTER PRODRUGS OF CORTICO-STEROIDS. Patent dated Apr. 17, 1984. Disclaimer filed June 22, 1984, by the assignee, *the Upjohn Co.*

Hereby enters this disclaimer to claims 1 through 12 of said patent.
[*Official Gazette January 8, 1985.*]